United States Patent [19]
Stoye et al.

[11] Patent Number: 6,100,034
[45] Date of Patent: Aug. 8, 2000

[54] DETECTION OF RETROVIRAL SUBTYPES BASED UPON ENVELOPE SPECIFIC SEQUENCES

[75] Inventors: Jonathan P. Stoye, Herts; Robin A. Weiss, London, both of United Kingdom

[73] Assignee: Medical Research Council, London, United Kingdom

[21] Appl. No.: 09/111,085

[22] Filed: Jul. 7, 1998

Related U.S. Application Data

[63] Continuation of application No. PCT/GB98/01428, May 18, 1998.

[30] Foreign Application Priority Data

May 16, 1997 [GB] United Kingdom .................. 9710154

[51] Int. Cl.$^7$ .............................. C12Q 1/68; C07H 21/02; C07H 21/04; C12N 15/00
[52] U.S. Cl. ........................... 435/6; 536/23.1; 536/24.3; 935/76; 935/77; 935/78
[58] Field of Search .................................. 536/23.1, 24.3, 536/23.2, 24.32, 23.7, 23.72; 435/6, 91.2

[56] References Cited

FOREIGN PATENT DOCUMENTS

| 0 184 187 | 12/1985 | European Pat. Off. . |
|---|---|---|
| 0 239 400 B1 | 3/1987 | European Pat. Off. . |
| 2188 638 | 10/1987 | United Kingdom . |
| WO 93/11161 | 6/1993 | WIPO . |
| WO 94/13804 | 6/1994 | WIPO . |
| WO 97/21836 | 6/1997 | WIPO . |
| WO 97/40167 | 10/1997 | WIPO . |

OTHER PUBLICATIONS

Bird, et al., *Science*, 242:423 (1988).
Cosset, et al., *J. Virol.*, 69:(10)6314 (1995).
Cosset, et al., *J.I Virol.*, 69(12):7430 (1995).
Ferry, et al., *Proc. Natl. Acad. Sci. USA*, 88:8377 (1991).
Frohman and Martin, *Techinique*, 1:165 (1989).
Holliger, et al., *Proc. Natl. Acad. Sci. USA*, 90;6444 (1993).
Huston, et al., *Proc. Natl. Acad. Sci. USA*, 85:5879 (1988).
Patience, et al., *Nature Medicine*, 3(3):282 (1997).
Tailor, et al.,*J. Virol.*, 67(11):6737 (1992).
Tristem, et al.,*J. Virol.*, 70(11):8241 (1996).
Hoopes et al., 1997, Molecular Screening of Xenodonor Genomes for Species–Specific Endogenous Retroviral DNA Sequences, Transplantation Proceedings, 29:897–898.
Le Tissier et al., 1997, Two sets of human–tropic pig retrovirus, Nature, 389: 681–682.
Stoye & Coffin, 1995, The dangers of xenotransplantation, Nature Medicine, 1: 1100.
Akiyoshi et al., Identification of a Full–Length cDNA for an Endogenous Retrovirus of Miniature Swine. J. of Virology 72 (5) : 4503–4507 (May 1998).

*Primary Examiner*—W. Gary Jones
*Assistant Examiner*—Ethan Whisenant
*Attorney, Agent, or Firm*—Banner & Witcoff, Ltd.

[57] ABSTRACT

The present invention is based upon the finding that porcine endogenous retroviruses exist in two different subtypes, which we have termed PERV-A and PERV-B. The differences are reflected in sequence divergence in the envelope genes, and these differences may be used to provide nucleic acid and antibody probes which can distinguish between the two subtypes. This allows patterns of subtype transmission between cells, particularly porcine to human cells, to be monitored.

27 Claims, 11 Drawing Sheets

```
              250        260        270        280        290        300
PERV-A  CCGATTCGGGGTGGAAAAGACCGAAAAGACTGAAAATCCCCTTAAGCTTCGCCTCCATCGCG
              960        970        980        990       1000
PERV-B  .....C................G......................................C 310        320        330        340        350        360
PERV-A  TGGTTCCTTACTCTGTCAATAACTCCTCAAGTAAATGGTAAACGCCTTGTGGACAGCCCG
             1020       1030       1040       1050       1060
PERV-B  .........AA...........C..G.CC.G.A..........A.A.......T..

370        380        390        400        410        420
PERV-A  AACTCCCATAAACCCTTATCTCTCACCTGGTTACTTACTGACTCCGGGTACAGGTATTAAT
             1080       1090       1100       1110       1120
PERV-B  .C......G....T......C..T......C.GA...T....C.T.A...G..G.C.C.
```

```
          430       440       450       460       470       480
PERV-A    ATTAACAGCACTCAAGGGGAGGCTCCCTTGGGACCTGGTGGCCTGAATTATATGTCTGC
                   1140      1150      1160      1170      1180
PERV-B    G.A..T.......G...T.TT.....TAGA..C...........C.GC..T......

490       500       510       520       530       540
PERV-A    CTTCGATCAGTAATCCCTGGTCTCAATGACCAGGCCACACCCCCGATGTACTCCGTGCT
                   1200      1210      1220      1230
PERV-B    ..C.....TGA.T.A...C.C.G.T..-.--.----....T...A.CC..G.....AG.

550       560       570       580       590       600
PERV-A    TACGGGGTTTTACGTTTGCCCAGGACCCCCAAATAATGAAGAATATTGTGGAAATCCTCAG
                   1240      1250      1260      1270      1280
PERV-B    ..T.....C..TTGC.........---.A..G.G..A..GA....C.....GGG.T..GG.

610       620       630       640       650       660
PERV-A    GATTTCTTTTGCAAGCAATGGAGCTGCATAACTTCTAATGATGGGAATTGGAAATGGCCA
                   1300      1310      1320      1330      1340
PERV-B    ..A.C...C..T.G.AG...........G.C..C..C......AG.C...........G
```

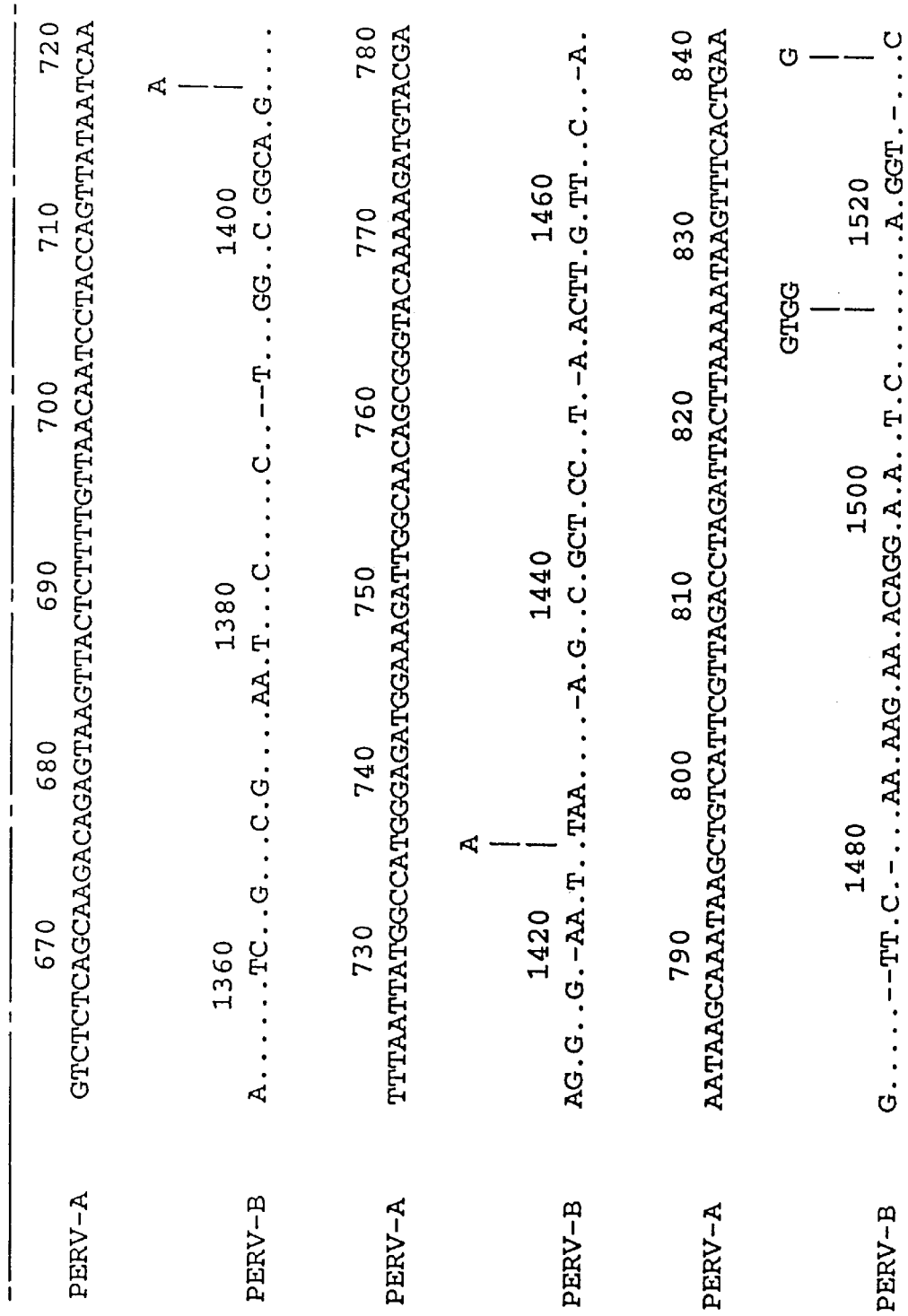
FIG. 1b(CONTD.)

```
PERV-A  1090       1100       1110       1120       1130       1140
        CCCACTGAGCCTAACATCACTATTAAAACAGGGGCGAAACTTTTTAGCCTTCATCCAGGGA

CAC AGA TCCCCAGGT
               ——— ——— ———
        1760       1800       1820
PERV-B  ..T..CA........G.TC..G.....ACA..G....C..C..T..............

1150       1160       1170       1180       1190       1200
PERV-A  GCTTTTCAAGCTCTCTTAACTCCAGGACTCCAGAGGCTACCTCTTCTTGTTGGCTTTGCTTA

C
                              ——
                    1840          1860         1880
PERV-B  .......C......CA.C............-..T..T..C..T...........TC...

1210       1220       1230       1240       1250       1260
PERV-A  GCTTCGGGCCCCACCTTACTATGAGGGAATGGCTAGAGAGGGAAATTCAATGTGACAAAG 1900       1920       1940
PERV-B  T.C..A..G..T........G........A....A....A.............C...A
```

```
          1270      1280      1290      1300      1310      1320
PERV-A  GAACATAGAGACCAATGTACATGGGGATCCCAAAATAAGCTTACCCTTACTGAGGTTTCT
          1960      1980      2000
PERV-B  ..G.......A.T...........G....G..............C......A......C 1330      1340      1350      1360      1370      1380
PERV-A  GGAAAAGGCACCTGCATAGGGATGGTTCCCCCATCCCACCAACACCTTTGTAACCACACT
          2020      2040      2060
PERV-B  ..G..G..G..A.......A.AA.C....................CT.TAGT...

1390      1400      1410      1420      1430      1440
PERV-A  GAAGCCTTTAATCGAACCTCTGAGAGTCAATATCTGGTACCTGGTTATGACAGGTGGTGG
          2080      2100      2120
PERV-B  .TG.TT.A.G.G.AGG....A...A.A...G....T.A..........

1450      1460      1470      1480      1490      1500
PERV-A  GCATGTAATACTGGATTAACCCCCTTGTGTTTTCCACCTTGGTTTCAACCAAACTAAAGAC
          2140      2160      2180
PERV-B  .....C........G.........C............CA..C.......T.C.....T
```

```
                1510       1520       1530       1540       1550       1560
                 |          |          |          |          |          |
PERV-A   TTTGCGTTATGGTCCAAATTGTCCCCGGGTGTACTACTATCCCGAAAAAGCAGTCCTT 2200       2210       2220       2230       2240
PERV-B   ...C..T..C............C...........A......C......T..GG...TG......

1570       1580       1590       1600       1610       1620
                 |          |          |          |          |          |
PERV-A   GATGAATATGACTATAGATATAATCGGCCAAAAAGAGAGCCCATATCCCTGACACTAGCT 2260       2270       2280       2290       2300
PERV-B   ...............C.G......C..A.............A...G.......T..C.......

1630       1640       1650       1660       1670       1680
                 |          |          |          |          |          |
PERV-A   GTAATGCTCTCGGATTGGGAGTGGCTGCTGCAGGCGTGGGAACAGGAACGGCTGCCCTAATCACA 2320       2330       2340       2350       2360
PERV-B   ..........A..GAC...C..TT......A.........G..A..........G........

1690       1700       1710       1720       1730       1740
                 |          |          |          |          |          |
PERV-A   GGACCGCAACAGCTGGAGAAAGGACTTAGTAACCTACATCGAATTGTAACGGAAGATCTC 2380       2390       2400       2410       2420
PERV-B   .....A..G.....A..............G..G.G......GCGGCCA.G..A.........

```
                1750       1760       1770       1780       1790       1800
PERV-A  CAAGCCCTAGAAAAATCTGTCAGTAACCTGGAGGAATCCCTAACCTCCTTATCTGAAGTG
                2440       2450       2460       2470       2480
PERV-B  .G.....T.....GG.G.....T..C.....A..A..G......G..T..T..G.........

1810       1820       1830       1840       1850       1860
PERV-A  GTTCTACAGAACAGAAGGGGTTAGATCTGTTATTTCTAAAAGAAGGAGGGTTATGTGTA
                2500       2510       2520       2530       2540
PERV-B  ..........C.G.....A..........C.G.....G.........T..........C.

1870       1880       1890       1900       1910       1920
PERV-A  GCCTTAAAAGAGGAATGCTGCTTCTATGTAGATCACTCAGGAGCCATCAGAGACTCCATG
                2560       2570       2580       2590       2600
PERV-B  .........A.....T...........................................

1930       1940       1950       1960       1970       1980
PERV-A  AGCAAGCTTAGAGAAAGGTTAGAGAGGCGTCGAAGGGAAAGAGAGGCTGACCAGGGGTGG
                2620       2630       2640       2650       2660
PERV-B  ............................................................
```

```
              1990      2000      2010      2020      2030      2040
PERV-A  TTTGAAGGATGGTTCAACAGGTCTCCTTGGATGACCACCCTGCTTTCTGCTCTGACGGGG
              2680      2700      2720
PERV-B  ..........................A.................................

2050      2060      2070      2080      2090      2100
PERV-A  CCCCTAGTAGTCCTGCTCCCTGTTACTTACACAGTTGGGCCTTGCTTAATTAATAGGTTTGTT
              2740      2760      2780
PERV-B  ..............................................................

2110      2120      2130      2140      2150      2160
PERV-A  GCCTTTGTTAGAGAACGAGTGAGTGCAGTCCAGATCATGGTACTTAGGCAACAGTACCAA
              2800      2820      2840
PERV-B  ..............................................................

2170      2180      2190      2200      2210      2220
PERV-A  GGCCTTCTGAGCCCAAGGAGAAACTGACCTCTAGCCTTCCCAGTTCTAAGATTAGAACTAT
              2860      2880      2900
PERV-B  ..............................................................
```

```
              2230       2240       2250       2260       2270       2280
PERV-A    TAACAAGACAAGAAGTGGGGAATGAAAGGATGAAAATGCAACCTAACCCTCCCAGAACCC
                   2920       2940       2960
PERV-B    ............................................................

2290       2300       2310       2320       2330       2340
PERV-A    AGGAAGTTAATAAAAAGCTCTAAATGCCCCCGAATTCCAGACCCTGCTGGCTGCCAGTAA
                   2980       3000       3020
PERV-B    ............................................................

2350       2360       2370       2380       2390       2400
PERV-A    ATAGGTAGAAGTCACACTTCCTATTGTTCCAGGGCCTGCTATCCTGGCCTAAGTAAGAT
                   3040       3060       3080
PERV-B    ............................................................

2410       2420       2430       2440       2450       2460
PERV-A    AACAGGAAATGAGTTGACTAATCGCTTATCTGGATTCTGTAAAACCGACTGGCACCATAG
                   3100       3120       3140
PERV-B    ............................................................
```

DETECTION OF RETROVIRAL SUBTYPES BASED UPON ENVELOPE SPECIFIC SEQUENCES

This application is a continuation of PCT/GB98/01428 filed May 18, 1998.

The present invention relates to methods and products for the detection of porcine endogenous retroviruses.

There is currently much interest in the development of xenotransplantation of organs to meet the shortage of human organs available for transplant. Considerable progress has been made in developing transgenic animals, particularly pigs, whose organs have been modified to remove immunogenic surface antigens and/or to present human antigen, or to inhibit components of the human immune system. However while progress has been made on the immunological problems of xenotransplantation, relatively little research has been conducted on the risk of infection being transmitted to an organ recipient by the presence of endogenous pathogens in the donor organ.

Recently, Patience et al., Nature Medicine, 1997, 3;282–286, reported the results of a study of pig endogenous retroviruses (PERVs) in porcine cell lines. The authors demonstrated that two different pig kidney cell lines, PK15 and MPK, produced endogenous retroviruses and the PK15 retroviruses were capable of infecting a human cell line (kidney 293 cells). Analysis of the protease and reverse transcriptase genes of the retroviruses infecting these cell lines showed that there was about 95% sequence similarity at the amino acid level between isolates from the two cell lines. This information was used to design nucleic acid primers for the analysis of DNA from porcine tissue and the authors demonstrated that multiple PERV related sequences existed in such tissue and were expressed. The primers were specific for porcine PERVs and did not detect sequences in human or murine cells.

WO97/21836, published on Jun. 19, 1997, describes three porcine retrovirus isolates. These isolates are currently described as PERV-A and PERV-C, with SEQ ID NO:1 and SEQ ID NO:3 of WO97/21836 being of the PERV-C type, and SEQ ID NO:2 being of the PERV-A type.

WO97/40167, published on Oct. 30, 1997, describes a retrovirus isolate from the PK-15 porcine cell line. This isolate is currently described in the art as being of a PERV-B type. Figure 3 of WO97/40167 sets out a sequence with 3 open reading frames indicated to be the gag, pol and env genes of the retrovirus. Figure 1 of WO97/40167 sets out a shorter sequence with a 3' end which extends into the 5' region of the env gene. There are differences between the 3' end of Figure 1 and the corresponding region of Figure 3. The differences are attributed in WO97/40167 to improvements in carrying out and analysing the sequence obtained.

DISCLOSURE OF THE INVENTION

Prior to the present invention, it had not been appreciated that PERVs existed in different subtypes. Prior to the publication of WO97/21836 and WO97/40167 we surprisingly identified two subtypes of this virus, which we designated PERV-A and PERV-B. More surprisingly, although the majority of individual isolates from the PK15 cell line are PERV-A isolates (29/32 tested), our initial data indicated that human 293 cells infected with the virus are exclusively or almost exclusively of the PERV-B subtype. Thus although the primers used by Patience et al. are capable of detecting numerous PERV sequences in porcine tissue and cell lines, these primers do not distinguish between the two subtypes of PERV.

In the light of the present invention we believe that the sequence of Figure 1 of WO97/40167 is derived from a PERV-A isolate, since the FIG. 1 sequence in the region of difference is substantially similar to the corresponding portion of the PERV-A isolate described herein.

In a first aspect the present invention thus provides an isolated nucleic acid probe, said probe being capable of hybridising to the PERV-B env gene under conditions in which said probe is substantially unable to hybridise to the PERV-A env gene. This is referred to below as a PERV-B specific probe (or "primer" or "oligonucleotide"). The terms "probe", "primer" and "oligonucleotide" are used synonymously.

In a second aspect, the invention provides an isolated nucleic acid probe, said probe being capable of hybridising to the PERV-A env gene under conditions in which said probe is substantially unable to hybridise to the PERV-B env gene. This is referred to below as a PERV-A specific probe (or "primer" or "oligonucleotide").

Although the env gene sequences are shown as the positive strand, it is to be understood that probes of the invention may be directed to either strand where integrated or cDNA retroviral sequences are to be detected. Where retroviral RNA is to be detected, a probe capable of hybridising to the positive strand is required (in the case of PCR initially to make cDNA).

In a further aspect, the invention provides a pair of primers suitable for conducting a polymerase chain reaction, at least one of said primers being a nucleic acid as defined above specific for the PERV-A or PERV-B genes. The probes and primers of the invention may be used in a method of detecting retroviruses in a sample of porcine or human tissue. Such tissue includes primary porcine tissue and human cell lines which have been cultivated in the presence of a porcine cell line, or human tissues which are from a human patient who has received a xenotransplant. Nucleic acid (e.g. mRNA, total RNA, DNA or total nucleic acid) from the tissues or cells may be probed directly or if desired retroviral sequences may be amplified using primers suitable for amplifying retroviral sequences in general (e.g. LTR primers) prior to detecting PERV env sequences of the invention, thus allowing those of skill in the art to distinguish between the PERV-A and PERV-B subtypes. The nucleic acid may be present in a sample comprising human or porcine tissue or cells, or may be cloned nucleic acid from such sources.

The differences between the two genes is reflected by changes to the env proteins, and these differences are believed to include differences to antigenic determinants (referred to herein as epitopes) in the two subtypes of proteins, which thus allows the development of antibodies which are capable of binding to an epitope on the PERV-B env protein under conditions where they are substantially unable to bind to the PERV-A env protein, and vice versa. These antibodies may be used in a method of detecting the presence of a pig endogenous retrovirus in porcine or human tissue or cell lines, thus allowing those of skill in the art to distinguish between the PERV-A and PERV-B subtypes.

DETAILED DESCRIPTION OF THE INVENTION

Our prototype isolate of the PERV-A env gene region is shown in SEQ ID NO. 1, and the envelope polypeptide encoded by nucleotides 211 to 2190 of SEQ ID NO. 1 is shown as SEQ ID NO. 2. For the purposes of the present invention, the PERV-A env gene is at least 80%, preferably at least 90% and more preferably at least 95% homologous to the coding sequence of SEQ ID NO. 1. Homologous sequences include those which encode the same polypeptide shown in SEQ ID NO:2 but differ from SEQ ID NO:1 due to the degeneracy of the genetic code.

The percentage homology (also referred to as identity) of DNA sequences can be calculated using commercially available algorithms, such as Lasergene software from DNAS-TAR Inc. or the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions.

Similarly, our prototype isolate of the PERV-B env gene region is shown in SEQ ID NO. 3, and the envelope polypeptide encoded by nucleotides 911 to 2881 of SEQ ID NO. 3 is shown as SEQ ID NO. 4. For the purposes of the present invention, the PERV-B env gene is at least 80%, preferably at least 90% and more preferably at least 95% homologous to the coding sequence of SEQ ID NO. 3. Homologous sequences include those which encode the same polypeptide shown in SEQ ID NO:4 but differ from SEQ ID NO:3 due to the degeneracy of the genetic code.

BRIEF DESCRIPTION OF THE DRAWINGS

An alignment of SEQ ID NO. 1 and SEQ ID NO. 3 is shown in FIGS. 1A–1F.

The PERV-B specific probe of the invention is preferably derived from the 5' end of the env gene of PERV-B, particularly from the region of PERV-B corresponding to nucleotides 1000 to 2500 of the SEQ ID NO. 3 isolate. More preferably the region corresponds to nucleotides 1100 to 1900.

It is to be understood that "derived" means conceptually derived, and physical isolation of the nucleic acid from the gene (as opposed to, for example, de novo synthesis) is not necessary.

Specific PERV-B probes include oligonucleotides consisting of a contiguous sequence of from 10 to 40 nucleotides of a PERV-B isolate derived from the sequence of SEQ ID NO:3 from 1000 to 2500, preferably 1100 to 1900, or the complement thereof. Such oligonucleotides include SEQ ID NO:7 (1376–1395 of SEQ ID NO:3) and SEQ ID NO:8 (complement of 1620–1639 of SEQ ID NO:3) shown in Example 3 below comprise 8 and 14 differences respectively in their sequences and the corresponding regions of SEQ ID NO:1 as follows:

```
PERV-B 5' TTCTCCTTTGTCAA--TTCCGG 3'   (SEQ ID NO:7)
           *   *    *  ***   **

PERV-A 5' TACTCTTTTGTTAACAATCCTA 3'   (SEQ ID NO:9)

and:

PERV-B 5' TACTTTATCGGGTCCCACTG 3'    (SEQ ID NO:8)
          * * *** * ********

PERV-A 5' TATTCTGAGGCGCGAATAGT 3'    (SEQ ID NO:10)
```

Figure 1A:
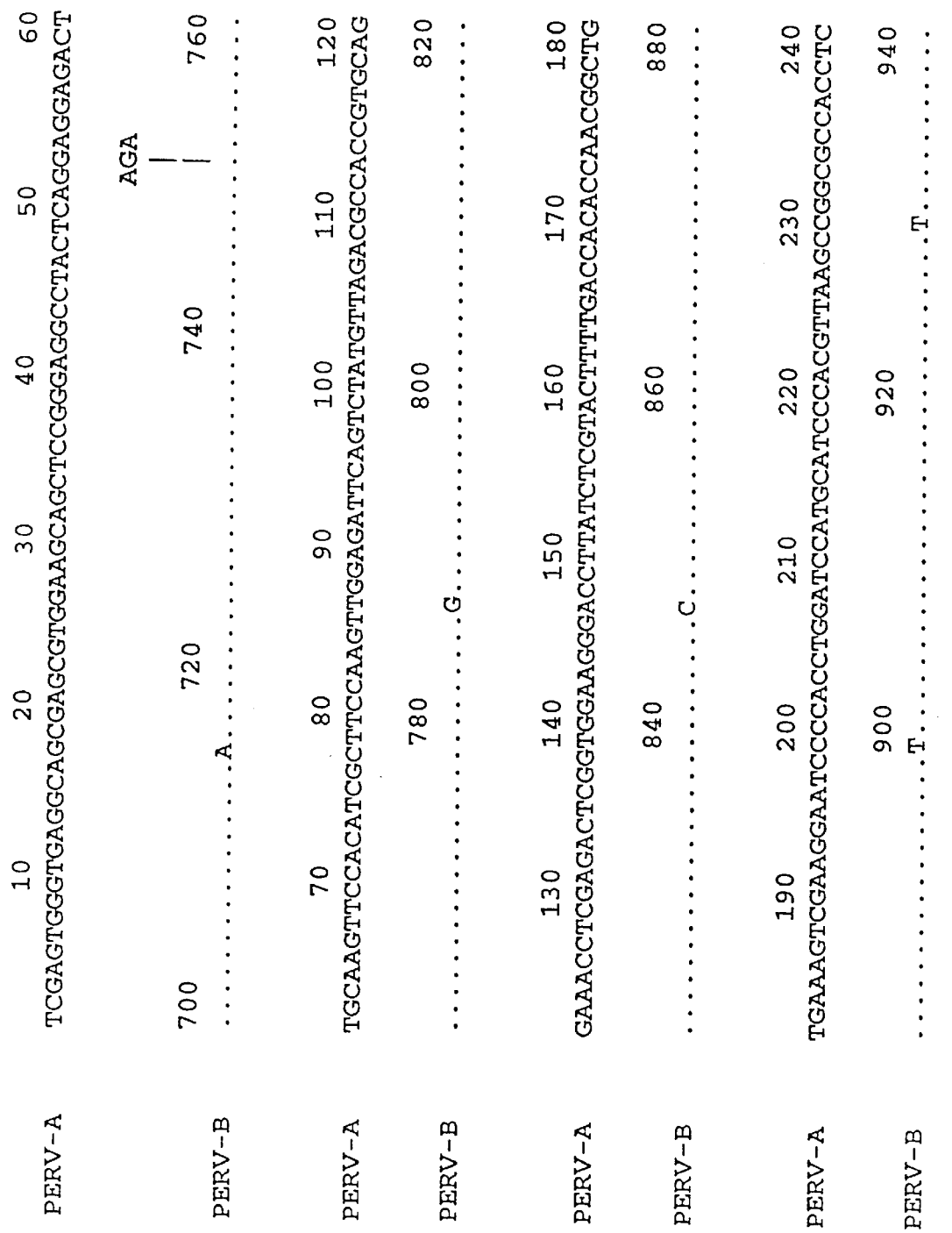
Figure 1C:
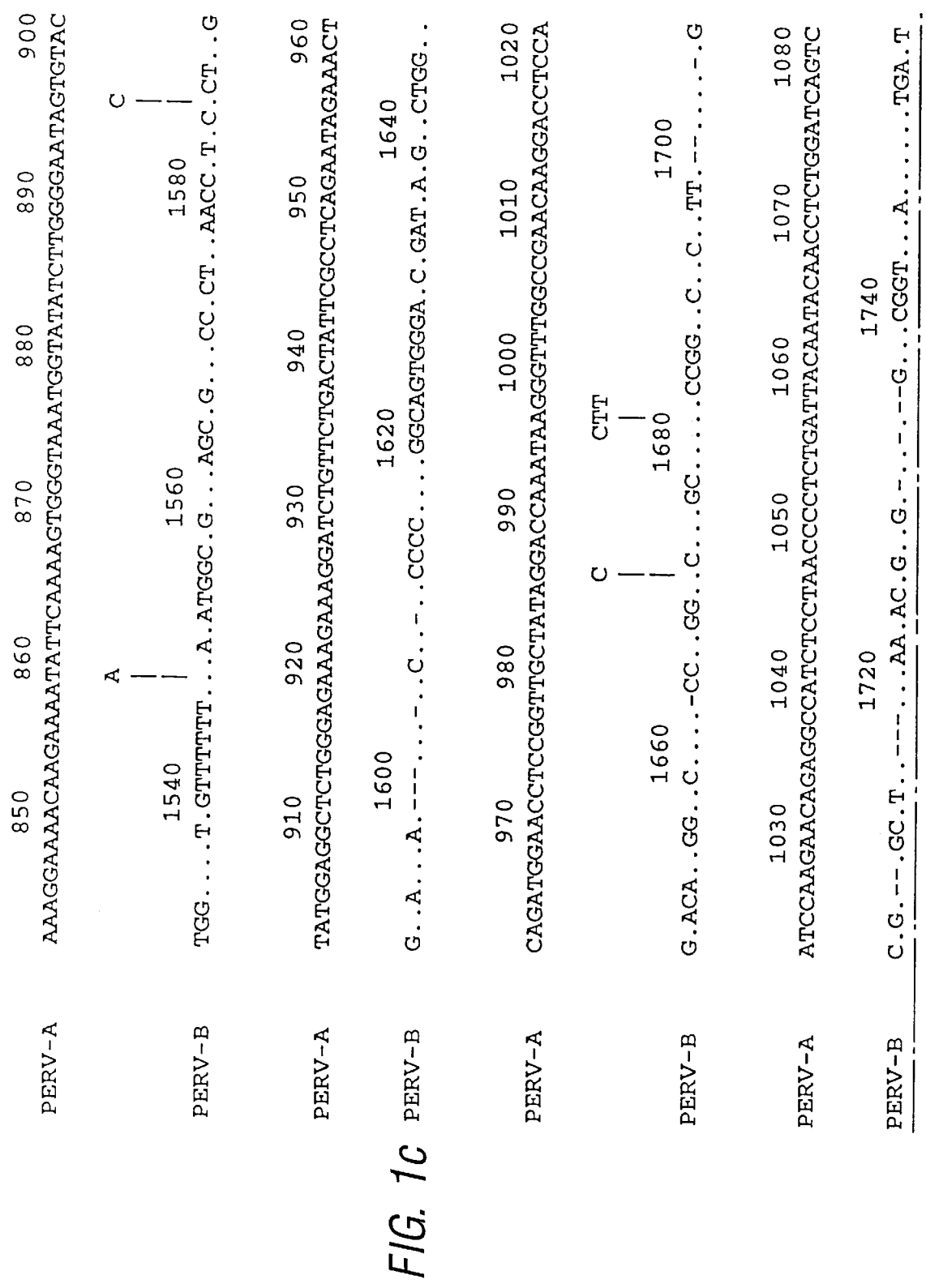

Similarly, the PERV-A specific probe of the invention may be derived from the regions shown in FIG. 1 which correspond to the abovementioned preferred and most preferred regions of PERV-A. Thus PERV-A specific probes include oligonucleotides consisting of a contiguous sequence of from 10 to 40 nucleotides of a PERV-A isolate derived from the sequence of SEQ ID NO:1 from 300 to 1809, preferably 400 to 1209, or the complement thereof.

Thus for example such oligonucleotides include SEQ ID NO:5 (742–760 of SEQ ID NO:1) and SEQ ID NO:6 (complement of 1082–1101 of SEQ ID NO:1) shown in Example 3 below. These comprise 10 and 21 differences respectively in their sequences and the corresponding regions of SEQ ID NO:3.

By "differences", it is meant substitutions, deletions and insertions. As can be seen from FIG. 1, the primers of SEQ ID NOs:5–8 include between them all these differences from the corresponding portions of the reference isolate.

The above-mentioned probes may additionally include, at their 3' and/or 5' termini, linker sequences (typically of from 3 to 8 nucleotides) of non-PERV-B or -A sequence. Linker sequences include those containing a restriction enzyme recognition sequence allowing the oligonucleotides to be introduced into or excised from a cloning or expression vector.

Nucleic acid probes of the invention may be obtained by first of all comparing the PERV-A and PERV-B sequences of FIG. 1 (or of other PERV-A and PERV-B isolates) and regions of the sequences which are sufficiently different to provide specific probes determined. This may be done by any suitable means, for example by calculating the predicted Tm of a probe when annealed to a specific region of the PERV-A or PERV-B sequences using a suitable algorithm or empirically by experiment. When by experiment this can be achieved by blotting the PERV-A and PERV-B sequences onto a nitrocellulose filter and probing the filter with a labelled putative probe under hybridising conditions. Probes of the invention will be able to hybridise to the PERV sequence of choice and not to the other PERV sequence under those conditions. Thus a PERV-B specific probe of the invention will be capable of hybridising to the sequence of SEQ ID NO:3 under conditions in which the probe does not hybridise to SEQ ID NO:1. Similarly, a PERV-A specific probe of the invention will be capable of hybridising to the sequence of SEQ ID NO:1 under conditions in which it does not hybridise to SEQ ID NO:3.

Hybridisation conditions will be selected to be commensurate with the size of the probe and can be determined by reference to standard text books such as Sambrook et al., Molecular Cloning, 1989, Cold Spring Harbour.

It will be understood by those of skill in the art that hybridisation conditions will vary depending upon whether a probe of the invention is hybridised to nucleic acid fixed to a solid support or is hybridised to a target nucleic acid in a liquid phase. In the case of the former (e.g. Southern or Northern blotting) a probe of the invention will be annealed under low stringency conditions and subsequently washed under high stringency conditions such that the probe will remain annealed to its target PERV sequence and not to the corresponding sequence of the other subtype. Where a probe of the invention is for use as a PCR primer annealing conditions will be selected in accordance with standard protocols such that the probe will hybridise to its target subtype nucleic acid and not to non-target subtype nucleic acid. Thus it will be understood that reference to hybridisation of a probe to target nucleic acid includes hybridisation achieved by blotting and washing on a solid phase as well as annealing in a liquid phase. In either case, the person of skill in the art will be able to test using routine skill and knowledge whether any selected sequence derived from a PERV-B env gene is able to hybridise to the PERV-B env nucleic acid under conditions in which it is substantially unable to hybridise to PERV-A env nucleic acid, and vice versa.

One way to calculate Tm of a probe is by reference to the formula for calculating the Tm of probes to a homologous target sequence. This formula is Tm(° C.)=2(A+T)+4(G+C)−5. This will provide the Tm under conditions of 3×SSC and 0.1% SDS (where SSC is 0.15M NaCl, 0.015M sodium citrate. pH 7). This formula is generally suitable for probes of up to 30 nucleotides in length. In the present invention, this formula may be used as an algorithm to calculate a nominal Tm of a probe for a specified sequence based upon the number of matches to its PERV target (e.g. PERV-B) sequence and PERV non-target sequence (e.g. PERV-A). For example, for the probe of SEQ ID NO:7 has a Tm of ((2×11)+(4×9)−5)=53° C. The sequence of SEQ ID NO:7 is derived from SEQ ID NO:3 and thus will have this Tm when used as a probe for this sequence, subject to the usual experimental error. However when SEQ ID NO:7 is used as a probe for the corresponding region of SEQ ID NO:1 (represented above as SEQ ID NO:9), the calculated Tm will be ((2×9)+(4×5)−5)=33° C., based on counting the number of matches. (Since for the purposes of the present invention the above formula is used as an algorithm, the actual Tm of probes when hybridised to non-complementary targets which do not exactly match the probe sequence may or may not correspond to the calculated value.)

Thus in a preferred aspect, a PERV-B specific probe will have a Tm (calculated as above) for SEQ ID NO:3 which is at least 5° C. higher than for SEQ ID NO:1, and vice versa for a PERV-A specific probe. Preferably the difference is at least 8° C., more preferably at least 10° C., at least 15° C. or at least 20° C.

The above formula generally useful for probes up to 30 nucleotides in length, but since it is used simply as an algorithm in the present invention, it may be extended to longer probes, for example up to 40 or even up to 50 nucleotides in length.

Suitable conditions for a probe to hybridise to a PERV target sequence may also be measured experimentally. Suitable experimental conditions comprise hybridising a candidate probe to both SEQ ID NO:1 and SEQ ID NO:3 on a solid support under low stringency hybridising conditions (e.g. 6×SSC at 55° C.), washing at reduced SSC and/or higher temperature, for example at 0.2×SSC at 45° C., and increasing the hybridisation temperature incrementally to determine hybridisation conditions which allow the probe to hybridise to SEQ ID NO:1 but not SEQ ID NO:3, or vice versa, as the case may be.

Although the hybridisation conditions used to distinguish between the PERV-B and PERV-A env genes should also be sufficient to distinguish over other "background" sequences present in human or porcine cells (particularly human and porcine genomic and mitochondrial sequences), it is also desirable that the probes do not, under such conditions, hybridise to such background sequences. This may also be determined by experiment, for example by blotting the probes to a solid support which carries at separate loci SEQ ID NO:1, SEQ ID NO:3 (for example cloned in plasmids), human total DNA and porcine total DNA.

The size of the probe may be selected by those of skill in the art taking account of the particular purposes the probes are to be used. Probes may be for example from 10 to 1000 nucleotides (or base pairs), e.g. from 50 to 500, such as from 200 to 500 nucleotides or base pairs. This size range is particularly suitable for Southern blots. However for some purposes, for example PCR, short oligonucleotide probes are preferred, generally in the size range of from 10 to 40 nucleotides in length, preferably 12 to 25 and more preferably from 18 to 24 such as 20, 21 or 22 nucleotides.

The probes may be labelled with a detectable label, including a radionuclide such as $^{32}P$ or $^{35}S$ which can be added to the probe using methods known per se in the art. The probe may alternatively carry a non-radioactive label such as biotin.

Generally, probes will be prepared by stepwise chemical synthesis, which is widely available commercially. Recombinant production of probes is also possible. Probes may be DNA or RNA, and may contain or consist of synthetic or modified nucleotides. A number of different types of modification to oligonucleotides are known in the art. These include methylphosphonate and phosphorothionate backbones, addition of acridine or polylysine chains at the 3' and/or 5' ends of the molecule. For the purposes of the present invention, it is to be understood that the probes and primers described herein may be modified by any method available in the art.

A preferred method of detection is by the polymerase chain reaction (PCR). This will involve PERV-B or PERV-A primer pairs, at least one of which is directed to PERV-B or PERV-A env gene sequences, the polarity of the probes being such that the region between them is amplified when the PCR is performed. At least one of each pair of PERV-A and/or PERV-B primers will be specific for its target PERV sequence. The other member of each pair may be targeted to non-env sequence or env sequence common to PERV-A and PERV-B. Preferably both members of a primer pair are specific for their target PERV sequence. Desirably the probes will be selected to amplify a region of the PERV-A and PERV-B of a convenient size to detect, such as between about 50 and 500, preferably between 150 and 400 nucleotides.

Where pairs of PERV-A and PERV-B primers are used in conjunction with each other, it is preferred that the primer pairs are selected such that different size PERV-A and PERV-B products are produced. Preferably the difference in size is at least from 5 to 50 base pairs, such as from 10 to 25 base pairs, so that detection of the products by electrophoresis on agarose gels by ethidium bromide staining may be conveniently carried out.

The methods of the invention which allow the PERV-A and PERV-B subtypes to be distinguished are useful in following the transmission of these viruses from porcine cells to other cell types, particularly human cells. In addition, the probes may be used to clone and characterize the different endogenous proviruses of pigs. Specific proviruses can be characterised by both their sequences and the genomic flanking sequences, and thus a map of the chromosomal locations of the viruses may be determined. The ability to distinguish between PERV-A and PERV-B proviruses will facilitate studies of the porcine endogenous retroviruses which might pose a threat to humans in a transplant setting.

The PERV-A and PERV-B nucleic acid sequences of the invention are novel and thus in a further aspect of the invention there is provided an isolated nucleic acid consisting essentially of the PERV-A or PERV-B env gene coding sequence, or a fragment thereof which is capable of hybridising to the PERV-B env gene under conditions in which said probe is substantially unable to hybridise to the PERV-A env gene, or vice versa. Vectors which comprise such sequences form a further aspect of the invention. The vector may be for replication of the sequence or for expression of the sequence in a suitable host cell. In such a case the vector will comprise a promoter operably linked to the env sequence, the promoter being compatible with the host cell which may be, for example, bacterial, e.g. E. coli, yeast, insect or mammalian, e.g. a CHO cell or a human cell line.

The env gene may be expressed in such a cell and recovered from the cell in substantially isolated form.

The differences in the PERV subtypes also allow the production of antibodies which can distinguish between the two subtypes. In a manner analogous to the production of probes, the sequence differences between the proteins of SEQ ID NO. 2 and SEQ ID NO. 4 can be examined, and suitable epitopes which reflect these differences determined using computer algorithms or by epitope scanning techniques. Monoclonal antibodies raised against these epitopes may be used to detect the presence of the PERV-A and/or PERV-B subtypes in a specific manner.

In a manner analogous to the nucleic acid probes, the antibodies are preferably directed to epitopes in the N-terminal region of the PERV-A and PERV-B env proteins, particularly epitopes encoded within the preferred regions identified above.

For the purposes of the present invention the term antibody describes an immunoglobulin whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544–546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., Science, 242, 423–426, 1988; Huston et al., PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P. Holliger et al. Proc. Natl. Acad. Sci. USA 90 6444–6448, 1993).

The reactivities of antibodies to an epitope in a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

A radionuclide such as $^{125}$I, $^{111}$In or $^{99m}$Tc may be attached to an antibody and these nuclides are useful in imaging target antigens in the body. Antibodies labelled with these labels may be used to examine xenotransplanted organs in a human recipient for the presence of PERVs as part of ongoing monitoring following transplantation.

Antibodies of the invention may be produced by conventional hybridoma technology, e.g. by linking a peptide comprising a suitable epitope to a carrier protein, injecting the linked peptide into an animal such as a rat or rabbit, recovering the spleen and producing hybridoma cell lines which are screened against the peptide for specific binding.

Antibodies may also be prepared by screening against synthetic libraries such as phage display libraries. Antibodies may also be made against the entire env protein or substantial parts thereof, and then screened individually against PERV-A and PERV-B env protein for specific binding to one or the other.

In one aspect of the invention a specific PERV-A antibody and a specific PERV-B antibody are used on parallel samples (or on the same sample where the two antibodies are labelled with different and distinguishable labels) to detect the presence of the two subtypes of retroviruses.

Antibodies specific for a PERV-B epitope will have at least a 100 fold higher affinity for that epitope than for the corresponding region (as indicated by alignments to the PERV-A sequence such as that of FIG. 1) of the PERV-A env protein, and vice versa. Desirably both types of specific antibodies will not cross react to other proteins normally present in human and porcine cells (i.e. have at least a 100 fold higher affinity to its target epitope than to such other proteins).

The probes, primers and antibodies of the invention may be used in all aspects of the development of porcine organ (e.g. kidney, liver, heart, pancreas, including tissues and cells therefrom, such as pancreatic islet cells) xenotransplantation. Thus the probes, primers and antibodies may be used to monitor the inheritance of human tropic viruses, thus facilitating the breeding of pigs lacking these viruses, particularly the PERV-B subtype. The invention will also be useful in monitoring the expression of the viruses in pigs and humans.

The following examples illustrate the invention.

EXAMPLE 1

Cloning of PERV-A and PERV-B Env Sequences cDNA clones were obtained using the 3' RACE technique (Frohman and Martin Technique 1:165–170, 1989). Total RNA from PK15, MPK and 293 cells was reverse transcribed to produce cDNA using an adapter primer dT-Ri-Ro.

A fraction of cDNA from PK15 and MPK cells was amplified by the polymerase chain reaction (PCR) using the primer PL146 (5'ATCCGTCGGCATGCATAATACGACTCAC, SEQ ID NO:11) in combination with PL135 (5'CGATTCAGTGCTGCTACAAC, SEQ ID NO:12) or PL137 (5'CCCTTATAACCTCTTGAGCG, SEQ ID NO:13). Products of approximately 6.5 kb were digested with XhoI and SphI and cloned into SalI//SphI digested pGem3Zf(+). Positive clones were identified and sequenced.

A portion of cDNA from 293 cells was amplified by PCR using primer PL137 in combination with primer Ro. Products of approximately 6.5 kb were isolated and digested with PstI and ligated with the pGem3Zf(+) plasmid digested with PstI and SmaI. After transformation into E. coli, positive clones were identified and sequenced.

Further clones were generated and sequenced from MPK and PK15 cDNA by amplification with primer PL147 (5'GTAATGCATGCTTCTATGGTGCCAGTCG, SEQ ID NO:14) in combination with either PL135, PL137 or PL148 (5'CTCTACGCATGCGTGGTGTACGACTGTG, SEQ ID NO:15) and digestion of products with XhoI/SphI or SphI and cloning into appropriately digested pGEM3Zf(+).

Further clones were generated and sequenced from 293 cDNA by PCR amplification with primer PL147 in combination with either PL135, PL137 or PL149 (5'GTAATCGGGTCAGACAATGG, SEQ ID NO:16) and digestion of products with EcoRI/PstI, PstI, or BamHI/EcoRI and cloning into appropriately digested pGem3Zf(+).

Oligos dT-Ri-Ro and Ro come from Frohman and Martin (Technique 1:165–170, 1989), PL146 is a modified version of Ro containing an additional SphI site, PL135 and PL137 were designed from the published PERV pol sequence (Tristan et al. J. Virol 70:8241–8246, 1996 Genbank ID X99933), PL147 and PL148 are PERV LTR primers derived from the sequences of our initial 293 clones.

Analysis of the clones identified two distinct subtypes, which we have termed PERV-A and PERV-B. An alignment of the two subtype envelope gene sequences is shown in FIG. 1.

EXAMPLE 2

Frequency of Full Length PERV-A and PERV-B Env Gene Isolation

The frequency of the subtypes in pig and human cells was analysed and the results are as follows:
1. From pig PK-15 cells
29/32 PERV-A
3/32 PERV-B
2. From human 293 cells infected with PK15 virus
0/18 PERV-A
18/18 PERV-B

EXAMPLE 3

Preparation of Specific Probes

1. PCR

Differences between the PERV-A and PERV-B subgroups allow the design of specific primers PL170 TGGAAAGATTGGCAACAGCG (SEQ ID NO:5)
PL171 AGTGATGTTAGGCTCAGTGG (SEQ ID NO:6)
PL172 TTCTCCTTTGTCAATTCCGG (SEQ ID NO:7)
PL173 TACTTTATCGGGTCCCACTG (SEQ ID NO:8)
PL170+PL171 are predicted to give a 361 base pair band with PERV-A;
PL172+PL173 are predicted to give a 264 base pair band with PERV-B.

PCR studies with cloned plasmid DNA confirmed these prediction and showed no cross-amplification between the two primer pairs. Sequencing the respective RT-PCR products from RNA containing both viral RNAs shows amplification only of the sequences predicted from each primer pair.

2. Southern Blot Probes

The amplification products of PL170+PL171 (361 bp, PERV-A probe) and PL172+PL173 (264 bp, PERV-B probe) show no cross hybridisation on plasmid blots. Both have been used on genomic southern blots.

EXAMPLE 4

Host Range Studies

The host range specified by the cloned PERV env genes were examined using a Moloney murine leukemia virus (Mo-MLV) based vector to deliver the β-galactosidase (lacZ) indicator gene to different cell types (Tailor et al. J. Virol. 67:6737–6741, 1993). The TELCeB6 cell line (Cosset et al. J. Virol. 69: 7430–7436, 1995) is derived from TE671 cells by stable transfection with CeB to supply the Mo-MLV gag-pol genes and carrying a modified lacZ gene (Ferry et al. PNAS 88: 8377–8381, 1991) in proviral context introduced by infection using an amphotropic viral vector. The PERV env genes were introduced by transfection of TELCeB6 cells with expression constructs derived from pFBMOSALF (Cosset et al. J. Virol, 69: 6314–6322, 1995) in which the PERV sequences, on XbaI-ClaI fragments, replace the corresponding Mo-MLV envelope sequence. Virus produced by transiently and stably transfected TELCeB6 cells were assayed for transfer of LacZ on 293, TE671 (human) and PK-15, PAE, ST-IOWA (pig) cells. Transfer of retroviral particles comprising the PERV-B envelope to human cells was demonstrated.

The infectious titre (LacZ positives/ml supernatant) was as follows:

| Virus | Pig (ST-IOWA) | Mink (Mu-1-lv) | Human (293) | Human (TE671) |
|---|---|---|---|---|
| PERV-A | 2000 | 1000 | 300 | 2000 |
| PERV-B | 800 | 4000 | 800 | 700 |

SEQUENCE LISTING

```
<160> NUMBER OF SEQ ID NOS: 16

<210> SEQ ID NO 1
<211> LENGTH: 2462
<212> TYPE: DNA
<213> ORGANISM: Porcine retrovirus

<400> SEQUENCE: 1
tcgagtgggt gaggcagcga gcgtggaagc agctccggga ggcctactca ggaggagact      60
tgcaagttcc acatcgcttc caagttggag attcagtcta tgttagacgc caccgtgcag     120
gaaacctcga gactcggtgg aagggacctt atctcgtact tttgaccaca ccaacggctg     180
tgaaagtcga aggaatcccc acctggatcc atgcatccca cgttaagccg gcgccacctc     240
ccgattcggg gtggaaagcc gaaaagactg aaaatcccct taagcttcgc ctccatcgcg     300
tggttcctta ctctgtcaat aactcctcaa gttaatggta aacgccttgt ggacagcccg     360
aactcccata aaccctttatc tctcacctgg ttacttactg actccggtac aggtattaat     420
attaacagca ctcaagggga ggctcccttg gggacctggt ggcctgaatt atatgtctgc     480
cttcgatcag taatccctgg tctcaatgac caggccacac cccccgatgt actccgtgct     540
tacgggtttt acgtttgccc aggaccccca aataatgaag aatattgtgg aaatcctcag     600
gatttctttt gcaagcaatg gagctgcata acttctaatg atgggaattg gaaatggcca     660
gtctctcagc aagacagagt aagttactct tttgttaaca atcctaccag ttataatcaa     720
tttaattatg gccatgggag atggaaagat tggcaacagc gggtacaaaa agatgtacga     780
aataagcaaa taagctgtca ttcgttagac ctagattact taaaaataag tttcactgaa     840
aaaggaaaac aagaaaatat tcaaaagtgg gtaaatggta tatcttgggg aatagtgtac     900
tatggaggct ctgggagaaa gaaaggatct gttctgacta ttcgcctcag aatagaaact     960
cagatggaac ctccggttgc tataggacca aataagggtt tggccgaaca aggacctcca    1020
atccaagaac agaggccatc tcctaacccc tctgattaca atacaacctc tggatcagtc    1080
cccactgagc ctaacatcac tattaaaaca ggggcgaaac ttttttagcct catccaggga    1140 gcttttcaag ctcttaactc cacgactcca gaggctacct cttcttgttg gctttgctta    1200
gcttcgggcc caccttacta tgagggaatg gctagaggag ggaaattcaa tgtgacaaag    1260
gaacatagag accaatgtac atggggatcc caaaataagc ttaccttac tgaggtttct    1320 ggaaaaggca cctgcatagg gatggttccc ccatcccacc aacacctttg taaccacact    1380
gaagccttta atcgaacctc tgagagtcaa tatctggtac ctggttatga caggtggtgg    1440
```

-continued

```
gcatgtaata ctggattaac cccttgtgtt tccaccttgg ttttcaacca aactaaagac      1500
ttttgcgtta tggtccaaat tgtccccegg gtgtactact atcccgaaaa agcagtcctt      1560
gatgaatatg actatagata taatcggcca aaagagagc ccatatccct gacactagct       1620
gtaatgctcg gatttgggagt ggctgcaggc gtgggaacag aacggctgc cctaatcaca     1680 ggaccgcaac agctggagaa aggacttagt aacctcatc gaattgtaac ggaagatctc      1740
caagccctag aaaatctgt cagtaacctg gaggaatccc taacctcctt atctgaagtg      1800
gttctacaga acagaagggg gttagatctg ttatttctaa aagaaggagg ttatgtgta      1860 gccttaaaag aggaatgctg cttctatgta gatcactcag gagccatcag agactccatg    1920
agcaagctta gagaaaggtt agagaggcgt cgaagggaaa gagaggctga ccaggggtgg    1980
tttgaaggat ggttcaacag gtctccttgg atgaccaccc tgctttctgc tctgacgggg   2040 ccctagtag tcctgctcct gttacttaca gttgggcctt gcttaattaa taggtttgtt     2100
gcctttgtta gagaacgagt gagtgcagtc cagatcatgt acttaggca acagtaccaa    2160 ggccttctga gccaaggaga aactgacctc tagccttccc agttctaaga ttagaactat   2220
taacaagaca agaagtgggg aatgaaagga tgaaaatgca acctaaccct cccagaaccc   2280
aggaagttaa taaaaagctc taaatgcccc cgaattccag accctgctgg ctgccagtaa    2340
ataggtagaa ggtcacactt cctattgttc cagggcctgc tatcctggcc taagtaagat    2400
aacaggaaat gagttgacta atcgcttatc tggattctgt aaaccgact ggcaccatag    2460 aa                                                                    2462
```

<210> SEQ ID NO 2
<211> LENGTH: 660
<212> TYPE: PRT
<213> ORGANISM: Porcine retrovirus

<400> SEQUENCE: 2

```
Met His Pro Thr Leu Ser Arg Arg His Leu Pro Ile Arg Gly Gly Lys
  1               5                  10                  15

Pro Lys Arg Leu Lys Ile Pro Leu Ser Phe Ala Ser Ile Ala Trp Phe
             20                  25                  30

Leu Thr Leu Ser Ile Thr Pro Gln Val Asn Gly Lys Arg Leu Val Asp
         35                  40                  45

Ser Pro Asn Ser His Lys Pro Leu Ser Leu Thr Trp Leu Leu Thr Asp
     50                  55                  60

Ser Gly Thr Gly Ile Asn Ile Asn Ser Thr Gln Gly Glu Ala Pro Leu
 65                  70                  75                  80

Gly Thr Trp Trp Pro Glu Leu Tyr Val Cys Leu Arg Ser Val Ile Pro
                 85                  90                  95

Gly Leu Asn Asp Gln Ala Thr Pro Pro Asp Val Leu Arg Ala Tyr Gly
            100                 105                 110

Phe Tyr Val Cys Pro Gly Pro Asn Asn Glu Glu Tyr Cys Gly Asn
        115                 120                 125

Pro Gln Asp Phe Phe Cys Lys Gln Trp Ser Cys Ile Thr Ser Asn Asp
    130                 135                 140

Gly Asn Trp Lys Trp Pro Val Ser Gln Gln Asp Arg Val Ser Tyr Ser
145                 150                 155                 160

Phe Val Asn Asn Pro Thr Ser Tyr Asn Gln Phe Asn Tyr Gly His Gly
                165                 170                 175

Arg Trp Lys Asp Trp Gln Gln Arg Val Gln Lys Asp Val Arg Asn Lys
            180                 185                 190
```

```
Gln Ile Ser Cys His Ser Leu Asp Leu Asp Tyr Leu Lys Ile Ser Phe
        195                 200                 205

Thr Glu Lys Gly Lys Gln Glu Asn Ile Gln Lys Trp Val Asn Gly Ile
    210                 215                 220

Ser Trp Gly Ile Val Tyr Tyr Gly Gly Ser Gly Arg Lys Lys Gly Ser
225                 230                 235                 240

Val Leu Thr Ile Arg Leu Arg Ile Glu Thr Gln Met Glu Pro Pro Val
                245                 250                 255

Ala Ile Gly Pro Asn Lys Gly Leu Ala Glu Gln Gly Pro Pro Ile Gln
            260                 265                 270

Glu Gln Arg Pro Ser Pro Asn Pro Ser Asp Tyr Asn Thr Thr Ser Gly
        275                 280                 285

Ser Val Pro Thr Glu Pro Asn Ile Thr Ile Lys Thr Gly Ala Lys Leu
290                 295                 300

Phe Ser Leu Ile Gln Gly Ala Phe Gln Ala Leu Asn Ser Thr Thr Pro
305                 310                 315                 320

Glu Ala Thr Ser Ser Cys Trp Leu Cys Leu Ala Ser Gly Pro Pro Tyr
                325                 330                 335

Tyr Glu Gly Met Ala Arg Gly Gly Lys Phe Asn Val Thr Lys Glu His
            340                 345                 350

Arg Asp Gln Cys Thr Trp Gly Ser Gln Asn Lys Leu Thr Leu Thr Glu
        355                 360                 365

Val Ser Gly Lys Gly Thr Cys Ile Gly Met Val Pro Pro Ser His Gln
    370                 375                 380

His Leu Cys Asn His Thr Glu Ala Phe Asn Arg Thr Ser Glu Ser Gln
385                 390                 395                 400

Tyr Leu Val Pro Gly Tyr Asp Arg Trp Trp Ala Cys Asn Thr Gly Leu
                405                 410                 415

Thr Pro Cys Val Ser Thr Leu Val Phe Asn Gln Thr Lys Asp Phe Cys
            420                 425                 430

Val Met Val Gln Ile Val Pro Arg Val Tyr Tyr Pro Glu Lys Ala
        435                 440                 445

Val Leu Asp Glu Tyr Asp Tyr Arg Tyr Asn Arg Pro Lys Arg Glu Pro
    450                 455                 460

Ile Ser Leu Thr Leu Ala Val Met Leu Gly Leu Gly Val Ala Ala Gly
465                 470                 475                 480

Val Gly Thr Gly Thr Ala Ala Leu Ile Thr Gly Pro Gln Gln Leu Glu
                485                 490                 495

Lys Gly Leu Ser Asn Leu His Arg Ile Val Thr Glu Asp Leu Gln Ala
            500                 505                 510

Leu Glu Lys Ser Val Ser Asn Leu Glu Glu Ser Leu Thr Ser Leu Ser
        515                 520                 525

Glu Val Val Leu Gln Asn Arg Arg Gly Leu Asp Leu Leu Phe Leu Lys
    530                 535                 540

Glu Gly Gly Leu Cys Val Ala Leu Lys Glu Glu Cys Cys Phe Tyr Val
545                 550                 555                 560

Asp His Ser Gly Ala Ile Arg Asp Ser Met Ser Lys Leu Arg Glu Arg
                565                 570                 575

Leu Glu Arg Arg Arg Arg Glu Arg Glu Ala Asp Gln Gly Trp Phe Glu
            580                 585                 590

Gly Trp Phe Asn Arg Ser Pro Trp Met Thr Thr Leu Leu Ser Ala Leu
        595                 600                 605
```

```
Thr Gly Pro Leu Val Val Leu Leu Leu Leu Thr Val Gly Pro Cys
    610                 615                 620

Leu Ile Asn Arg Phe Val Ala Phe Val Arg Glu Arg Val Ser Ala Val
625                 630                 635                 640

Gln Ile Met Val Leu Arg Gln Gln Tyr Gln Gly Leu Leu Ser Gln Gly
                    645                 650                 655

Glu Thr Asp Leu
            660

<210> SEQ ID NO 3
<211> LENGTH: 3482
<212> TYPE: DNA
<213> ORGANISM: Porcine retrovirus

<400> SEQUENCE: 3
gcatgcctgc agcagttggt cagaacatcc ccttatcatg ttctgaggct accaggagtg      60
gctgactcgg tggtcaaaca ttgtgtgccc tgccagctgg ttaatgctaa tccttccaga    120
atacctccag gaaagagact aaggggaagc acccaggcg ctcactggga agtggacttc     180
actgaggtaa agccggctaa atacggaaac aaatatctat tggtttttgt agacaccttt    240
tcaggatggg tagaggctta tcctactaag aaagagactt caaccgtggt ggctaaaaaa    300
atactggagg aaattttttcc gagatttgga ataccttaagg taatcgggtc agacaatggt    360
ccagcttttg ttgcccaggt aagtcaggga ctggccaaga tattggggat tgattggaaa    420
ctgcattgtg catacagacc ccaaagctca ggacaggtag agaggatgaa tagaaccatt    480
aaagagaccc ttaccaaatt gaccacagag actggcatta atgattggat agctctcctg    540
ccctttgtgc tttttagggt taggaacacc cctggacagt ttgggctgac cccctatgaa    600
ttgctctacg ggggaccccc cccgttggta gaaattgctt ctgtacatag tgctgatgtg    660
ctgctttccc agcctctgtt ctctaggctc aaggcgctcg agtgggtgag gcaacgagcg    720
tggaagcagc tccgggaggc ctactcagga gaaggagact tgcaagttcc acatcgcttc    780
caagtgggag attcagtcta tgttagacgc accgtgcag gaaacctcga gactcggtgg    840
aagggcccctt atctcgtact tttgaccaca ccaacggctg tgaaagtcga aggaatctcc    900
acctggatcc atgcatccca cgttaagctg gcgccacctc ccgactcggg gtggagagcc    960
gaaaagactg agaatcccct taagcttcgc ctccatcgcc tggttcctta ctctaacaat   1020
aactccccag gccagtagta aacgccttat agacagctcg aacccccata gacctttatc   1080
ccttacctgg ctgattattg accctgatac gggtgtcact gtaaatagca ctcgaggtgt   1140
tgctcctaga ggcacctggt ggcctgaact gcatttctgc ctccgattga ttaaccccgc   1200
tgttaaaagc acacctccca acctagtccg tagttatggg ttctattgct gcccaggcac   1260
agagaaagag aaatactgtg ggggttctgg gaatccttc tgtaggagat ggagctgcgt    1320
cacctccaac gatggagact ggaaatggcc gatctctctc caggaccggg taaaattctc   1380
ctttgtcaat tccggcccgg gcaagtacaa agtgatgaaa ctatataaag ataagagctg   1440
ctcccccatca gacttagatt atctaaagat aagtttcact gaaaaaggaa acaggaaaa   1500
tattcaaaag tggataaatg gtatgagctg gggaatagtt tttttataaat atggcggggg   1560
agcagggtcc actttaacca ttcgccttag gatagagacg gggacagaac ccctgtggc   1620
agtgggaccc gataaagtac tggctgaaca ggggcccccg ccctggagc caccgcataa   1680
cttgccggtg ccccaattaa cctcgctgcg gcctgacata acacagccgc ctagcaacgg   1740
taccactgga ttgattccta ccaacacgcc tagaaactcc ccaggtgttc ctgttaagac   1800
```

-continued

```
aggacagaga ctcttcagtc tcatccaggg agctttccaa gccatcaact ccaccgaccc     1860
tgatgccact tcttcttgtt ggctttgtct atcctcaggg cctccttatt atgaggggat     1920
ggctaaagaa ggaaaattca atgtgaccaa agagcataga aatcaatgta catgggggtc     1980
ccgaaataag cttaccctca ctgaagtttc cgggaagggg acatgcatag gaaaagctcc     2040
cccatcccac caacacctt gctatagtac tgtggtttat gagcaggcct cagaaaatca      2100
gtatttagta cctggttata acaggtggtg ggcatgcaat actgggttaa cccctgtgt      2160 ttccacctca gtcttcaacc aatccaaaga tttctgtgtc atggtccaaa tcgtcccccg      2220
agtgtactac catcctgagg aagtggtcct tgatgaatat gactatcggt ataaccgacc     2280
aaaaagagaa cccgtatccc ttaccctagc tgtaatgctc ggattaggga cggccgttgg     2340
cgtaggaaca gggacagctg ccctgatcac aggaccacag cagctagaga aggacttgg      2400 tgagctacat gcggccatga cagaagatct ccgagcctta gaggagtctg ttagcaacct     2460
agaagagtcc ctgacttctt tgtctgaagt ggttctacag aaccggaggg gattagatct     2520
gctgtttcta agagaaggtg ggttatgtgc agccttaaaa gaagaatgtt gcttctatgt     2580
agatcactca ggagccatca gagactccat gagcaagctt agagaaaggt tagagaggcg     2640
tcgaagggaa agagaggctg accagggtg gtttgaagga tggttcaaca ggtctccttg      2700
gatgaccacc ctgctttctg ctctgacggg accctagta gtcctgctcc tgttacttac      2760
agttgggcct tgcttaatta ataggtttgt tgcctttgtt agagaacgag tgagtgcagt     2820
ccagatcatg gtacttaggc aacagtacca aggccttctg agccaaggag aaactgacct     2880
ctagccttcc cagttctaag attagaacta ttaacaagac aagaagtggg gaatgaaagg    2940
atgaaaatgc aacctaaccc tcccagaacc caggaagtta ataaaaagct ctaaatgccc     3000
ccgaattcca gaccctgctg gctgccagta aataggtaga aggtcacact tcctattgtt     3060
ccagggcctg ctatcctggc ctaagtaaga taacaggaaa tgagttgact aatcgcttat     3120
ctggattctg taaaaccgac tggcaccata gaagaattga ttacacattg acagccctag    3180
tgacctatct caactgcaat ctgtcactct gcccaggagc ccacgcagat gcggacctcc    3240
ggagctattt taaaatgatt ggtccacgga gcgcgggctc tcgatatttt aaaatgattg    3300
gtccacggag cgcgggctct tcgatatttt aaaatgattg gtttgtgacg cacaggcttt    3360
gttgtgaacc cataaaagc tgtcccgatt ccgcactcgg ggccgcagtc ctctacccct     3420
gcgtggtgta cgactgtggg ccccagcgcg cttggaataa aaatcctctt gctgtttgca    3480
tc                                                                    3482
```

<210> SEQ ID NO 4
<211> LENGTH: 657
<212> TYPE: PRT
<213> ORGANISM: Porcine retrovirus

<400> SEQUENCE: 4

```
Met His Pro Thr Leu Ser Trp Arg His Leu Pro Thr Arg Gly Gly Glu
 1               5                   10                  15

Pro Lys Arg Leu Arg Ile Pro Leu Ser Phe Ala Ser Ile Ala Trp Phe
             20                  25                  30

Leu Thr Leu Thr Ile Thr Pro Gln Ala Ser Ser Lys Arg Leu Ile Asp
         35                  40                  45

Ser Ser Asn Pro His Arg Pro Leu Ser Leu Thr Trp Leu Ile Ile Asp
     50                  55                  60
```

-continued

```
Pro Asp Thr Gly Val Thr Val Asn Ser Thr Arg Gly Val Ala Pro Arg
 65                  70                  75                  80

Gly Thr Trp Trp Pro Glu Leu His Phe Cys Leu Arg Leu Ile Asn Pro
             85                  90                  95

Ala Val Lys Ser Thr Pro Pro Asn Leu Val Arg Ser Tyr Gly Phe Tyr
            100                 105                 110

Cys Cys Pro Gly Thr Glu Lys Glu Lys Tyr Cys Gly Gly Ser Gly Glu
            115                 120                 125

Ser Phe Cys Arg Arg Trp Ser Cys Val Thr Ser Asn Asp Gly Asp Trp
        130                 135                 140

Lys Trp Pro Ile Ser Leu Gln Asp Arg Val Lys Phe Ser Phe Val Asn
145                 150                 155                 160

Ser Gly Pro Gly Lys Tyr Lys Val Met Lys Leu Tyr Lys Asp Lys Ser
                165                 170                 175

Cys Ser Pro Ser Asp Leu Asp Tyr Leu Lys Ile Ser Phe Thr Glu Lys
            180                 185                 190

Gly Lys Gln Glu Asn Ile Gln Lys Trp Ile Asn Gly Met Ser Trp Gly
            195                 200                 205

Ile Val Phe Tyr Lys Tyr Gly Gly Ala Gly Ser Thr Leu Thr Ile
        210                 215                 220

Arg Leu Arg Ile Glu Thr Gly Thr Glu Pro Val Ala Val Gly Pro
225                 230                 235                 240

Asp Lys Val Leu Ala Glu Gln Gly Pro Pro Ala Leu Glu Pro Pro His
                245                 250                 255

Asn Leu Pro Val Pro Gln Leu Thr Ser Leu Arg Pro Asp Ile Thr Gln
            260                 265                 270

Pro Pro Ser Asn Gly Thr Thr Gly Leu Ile Pro Thr Asn Thr Pro Arg
        275                 280                 285

Asn Ser Pro Gly Val Pro Val Lys Thr Gly Gln Arg Leu Phe Ser Leu
        290                 295                 300

Ile Gln Gly Ala Phe Gln Ala Ile Asn Ser Thr Asp Pro Asp Ala Thr
305                 310                 315                 320

Ser Ser Cys Trp Leu Cys Leu Ser Ser Gly Pro Pro Tyr Tyr Glu Gly
                325                 330                 335

Met Ala Lys Glu Gly Lys Phe Asn Val Thr Lys Glu His Arg Asn Gln
            340                 345                 350

Cys Thr Trp Gly Ser Arg Asn Lys Leu Thr Leu Thr Glu Val Ser Gly
            355                 360                 365

Lys Gly Thr Cys Ile Gly Lys Ala Pro Pro Ser His Gln His Leu Cys
        370                 375                 380

Tyr Ser Thr Val Val Tyr Glu Gln Ala Ser Glu Asn Gln Tyr Leu Val
385                 390                 395                 400

Pro Gly Tyr Asn Arg Trp Trp Ala Cys Asn Thr Gly Leu Thr Pro Cys
                405                 410                 415

Val Ser Thr Ser Val Phe Asn Gln Ser Lys Asp Phe Cys Val Met Val
            420                 425                 430

Gln Ile Val Pro Arg Val Tyr Tyr His Pro Glu Glu Val Val Leu Asp
        435                 440                 445

Glu Tyr Asp Tyr Arg Tyr Asn Arg Pro Lys Arg Glu Pro Val Ser Leu
        450                 455                 460

Thr Leu Ala Val Met Leu Gly Leu Gly Thr Ala Val Gly Val Gly Thr
465                 470                 475                 480

Gly Thr Ala Ala Leu Ile Thr Gly Pro Gln Gln Leu Glu Lys Gly Leu
```

```
                    485                 490                 495
Gly Glu Leu His Ala Ala Met Thr Glu Asp Leu Arg Ala Leu Glu Glu
                500                 505                 510

Ser Val Ser Asn Leu Glu Ser Leu Thr Ser Leu Ser Glu Val Val
        515                 520                 525

Leu Gln Asn Arg Arg Gly Leu Asp Leu Leu Phe Leu Arg Glu Gly Gly
        530                 535                 540

Leu Cys Ala Ala Leu Lys Glu Cys Cys Phe Tyr Val Asp His Ser
545                 550                 555                 560

Gly Ala Ile Arg Asp Ser Met Ser Lys Leu Arg Glu Arg Leu Glu Arg
                565                 570                 575

Arg Arg Arg Glu Arg Glu Ala Asp Gln Gly Trp Phe Glu Gly Trp Phe
            580                 585                 590

Asn Arg Ser Pro Trp Met Thr Thr Leu Leu Ser Ala Leu Thr Gly Pro
                595                 600                 605

Leu Val Val Leu Leu Leu Leu Thr Val Gly Pro Cys Leu Ile Asn
        610                 615                 620

Arg Phe Val Ala Phe Val Arg Glu Arg Val Ser Ala Val Gln Ile Met
625                 630                 635                 640

Val Leu Arg Gln Gln Tyr Gln Gly Leu Leu Ser Gln Gly Glu Thr Asp
                645                 650                 655

Leu

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
tggaaagatt ggcaacagcg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
agtgatgtta ggctcagtgg                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ttctcctttg tcaattccgg                                              20

<210> SEQ ID NO 8
<211> LENGTH: 20
<212> TYPE: DNA
<213> ORGANISM: Artificial Sequence
<220> FEATURE:
```

```
<223> OTHER INFORMATION: Description of Artificial Sequence:
      oligonucleotide

<400> SEQUENCE: 8
tactttatcg ggtcccactg                                                     20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
tactcttttg ttaacaatcc ta                                                  22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
tattctgagg cgcgaatagt                                                     20

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
atccgtcggc atgcataata cgactcac                                            28

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
cgattcagtg ctgctacaac                                                     20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
cccttataac ctcttgagcg                                                     20

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:
```

-continued

```
    oligonucleotide

<400> SEQUENCE: 14
gtaatgcatg cttctatggt gccagtcg                                       28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
ctctacgcat gcgtggtgta cgactgtg                                       28

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
gtaatcgggt cagacaatgg                                                20
```

What is claimed is:

1. An isolated nucleic acid probe which is capable of hybridising to SEQ ID NO:3 or the complement thereof under conditions in which it is not capable of hybridising to SEQ ID NO:1 or the complement thereof.

2. An isolated nucleic acid probe according to claim 1 which is derived from the region of PERV-B derived from nucleotides 1000 to 2500 of the SEQ ID NO. 3 isolate.

3. An isolated nucleic acid probe which is capable of hybridising to SEQ ID NO:1 or the complement thereof under conditions in which it is not capable of hybridising to SEQ ID NO:3 or the complement thereof.

4. An isolated nucleic acid according to claim 3 which is derived from the region of PERV-A derived from nucleotides 300 to 1809 of the SEQ ID NO:1 isolate.

5. An isolated nucleic acid probe according to claim 1 which is from 10 to 40 nucleotides in length.

6. A pair of primers suitable for conducting a polymerase chain reaction, at least one of said primers being a nucleic acid as defined in claim 1.

7. A pair of primers suitable for conducting a polymerase chain reaction, at least one of said primers being a nucleic acid as defined in claim 3.

8. A method of determining the subtype of a porcine endogenous retrovirus in a sample which contains or is suspected of containing one or both of the PERV-A and PERV-B subtypes, said method comprising probing said sample with a nucleic acid probe as defined in claim 2, and determining whether or not said probe detects either of said subtypes in said sample.

9. A method according to claim 8 wherein retroviral material from said sample is amplified prior to probing.

10. A method according to claim 8 wherein the sample is cloned nucleic acid obtained from pig or human cells.

11. A method according to claim 8 wherein the sample comprises tissue which is primary porcine tissue.

12. A method according to claim 8 wherein the sample is a human cell line which has been cultivated in the presence of a porcine cell line.

13. A method of determining the subtype of a porcine endogenous retrovirus in a sample which contains or is suspected of containing one or both of the PERV-A and PERV-B subtypes, said method comprising probing said sample with a nucleic acid probe as defined in claim 3, and determining whether or not said probe detects either of said subtypes in said sample.

14. The method of claim 13 wherein retroviral material from said sample is amplified prior to probing.

15. The method of claim 13 wherein the sample is cloned nucleic acid obtained from pig or human cells.

16. The method of claim 13 wherein the sample comprises tissue which is primary porcine tissue.

17. The method of claim 13 wherein the sample is a human cell line which has been cultivated in the presence of a porcine cell line.

18. A method of determining the subtype of a porcine endogenous retrovirus in a sample which contains or is suspected of containing one or both of the PERV-A and PERV-B subtypes, said method comprising subjecting said sample to a polymerase chain reaction using said pair of primers as claimed in claim 6, and determining whether or not said pair of primers detects either of said subtypes in said sample.

19. The method of claim 18 wherein retroviral material from said sample is amplified prior to said subjecting.

20. The method of claim 18 wherein the sample is cloned nucleic acid obtained from pig or human cells.

21. The method of claim 18 wherein the sample comprises tissue which is primary porcine tissue.

22. The method of claim 18 wherein the sample is a human cell line which has been cultivated in the presence of a porcine cell line.

23. A method of determining the subtype of a porcine endogenous retrovirus in a sample which contains or is suspected of containing one or both of the PERV-A and PERV-B subtypes, said method comprising subjecting said sample to a polymerase chain reaction using said pair of primers as claimed in claim 7, and determining whether or not said pair of primers detects either of said subtypes in said sample.

24. The method of claim 23 wherein retroviral material from said sample is amplified prior to said subjecting.

25. The method of claim 23 wherein the sample is cloned nucleic acid obtained from pig or human cells.

26. The method of claim 23 wherein the sample comprises tissue which is primary porcine tissue.

27. The method of claim 23 wherein the sample is a human cell line which has been cultivated in the presence of a porcine cell line.

\* \* \* \* \*